US006167883B1

(12) United States Patent
Beran et al.

(10) Patent No.: US 6,167,883 B1
(45) Date of Patent: Jan. 2, 2001

(54) MEDICAL AIR HOSE INTERNAL FLOW HEATER

(75) Inventors: Anthony V. Beran, Santa Ana; Gordon Shigezawa, Irvine; Morris Minch, Orange, all of CA (US)

(73) Assignee: Respiratory Support Products, Inc., Irvine, CA (US)

( * ) Notice: Under 35 U.S.C. 154(b), the term of this patent shall be extended for 0 days.

(21) Appl. No.: 09/012,249

(22) Filed: Jan. 23, 1998

(51) Int. Cl.[7] .................................................. A61M 16/00
(52) U.S. Cl. ....................................................... 128/203.17
(58) Field of Search ...................... 128/203.17, 204.17, 128/203.12, 203.27; 604/113

(56) References Cited

U.S. PATENT DOCUMENTS

| | | |
|---|---|---|
| 623,022 | 4/1899 | Johnson . |
| 1,572,300 | 2/1926 | Max . |
| 1,794,215 | 2/1931 | Titus . |
| 3,808,403 * | 4/1974 | Kanaya et al. ........................ 219/528 |
| 3,871,373 * | 3/1975 | Jackson ............................ 128/203.27 |
| 4,000,341 | 12/1976 | Matson . |
| 4,249,923 | 2/1981 | Walda . |
| 4,476,685 | 10/1984 | Aid . |
| 4,532,414 | 7/1985 | Shah et al. . |
| 4,543,474 * | 9/1985 | Horsma et al. ....................... 219/553 |
| 4,682,010 | 7/1987 | Drapeau et al. . |
| 4,686,354 | 8/1987 | Makin . |
| 4,705,508 | 11/1987 | Karnavas et al. . |
| 4,708,831 * | 11/1987 | Elsworth et al. ................ 128/203.27 |
| 4,773,410 * | 9/1988 | Blackmer et al. .............. 128/204.17 |
| 4,955,883 | 9/1990 | Nevyas et al. . |
| 4,962,761 | 10/1990 | Golden . |
| 4,967,744 * | 11/1990 | Chua ................................ 128/204.17 |
| 5,027,809 | 7/1991 | Robinson . |
| 5,106,373 | 4/1992 | Augustine et al. . |
| 5,154,661 | 10/1992 | Higgins . |
| 5,172,686 | 12/1992 | Anthony . |
| 5,180,896 | 1/1993 | Gibby et al. . |
| 5,246,438 | 9/1993 | Langberg . |
| 5,249,585 | 10/1993 | Turner et al. . |
| 5,269,749 | 12/1993 | Koturov . |
| 5,322,057 * | 6/1994 | Raabe et al. ..................... 128/203.12 |
| 5,357,948 | 10/1994 | Eilentropp . |
| 5,362,310 | 11/1994 | Semm . |
| 5,433,708 * | 7/1995 | Nichols et al. ....................... 604/113 |
| 5,460,628 | 10/1995 | Neuwirth et al. . |
| 5,462,048 * | 10/1995 | Lambert .......................... 128/201.13 |
| 5,492,529 | 2/1996 | Neuwirth et al. . |
| 5,537,996 * | 7/1996 | McPhee ........................... 128/204.17 |
| 5,862,303 * | 1/1999 | Adar et al. ............................ 392/472 |
| 5,964,223 * | 10/1999 | Baran .............................. 128/207.14 |

* cited by examiner

Primary Examiner—John G. Weiss
Assistant Examiner—V. Srivastava
(74) Attorney, Agent, or Firm—Price and Gess

(57) ABSTRACT

An improved medical conduit including a heating element for controlling the temperature and humidity of a gas to be delivered to a recipient patient is disclosed. A flexible ribbon spanning the width of a flexible tubing and extending generally the length of the tubing is provided, where the flexible ribbon carries a heating element therein. The heating element, preferably an electrically conductive wire or plurality of wires, is connected to a power supply in order to heat the flow of gas traveling within the tube. The flow is heated as it passes over and around the heating element. The flexible ribbon supporting the heating element can be integral with the tubing or comprise an insertable unit which fits into the tubing.

17 Claims, 2 Drawing Sheets

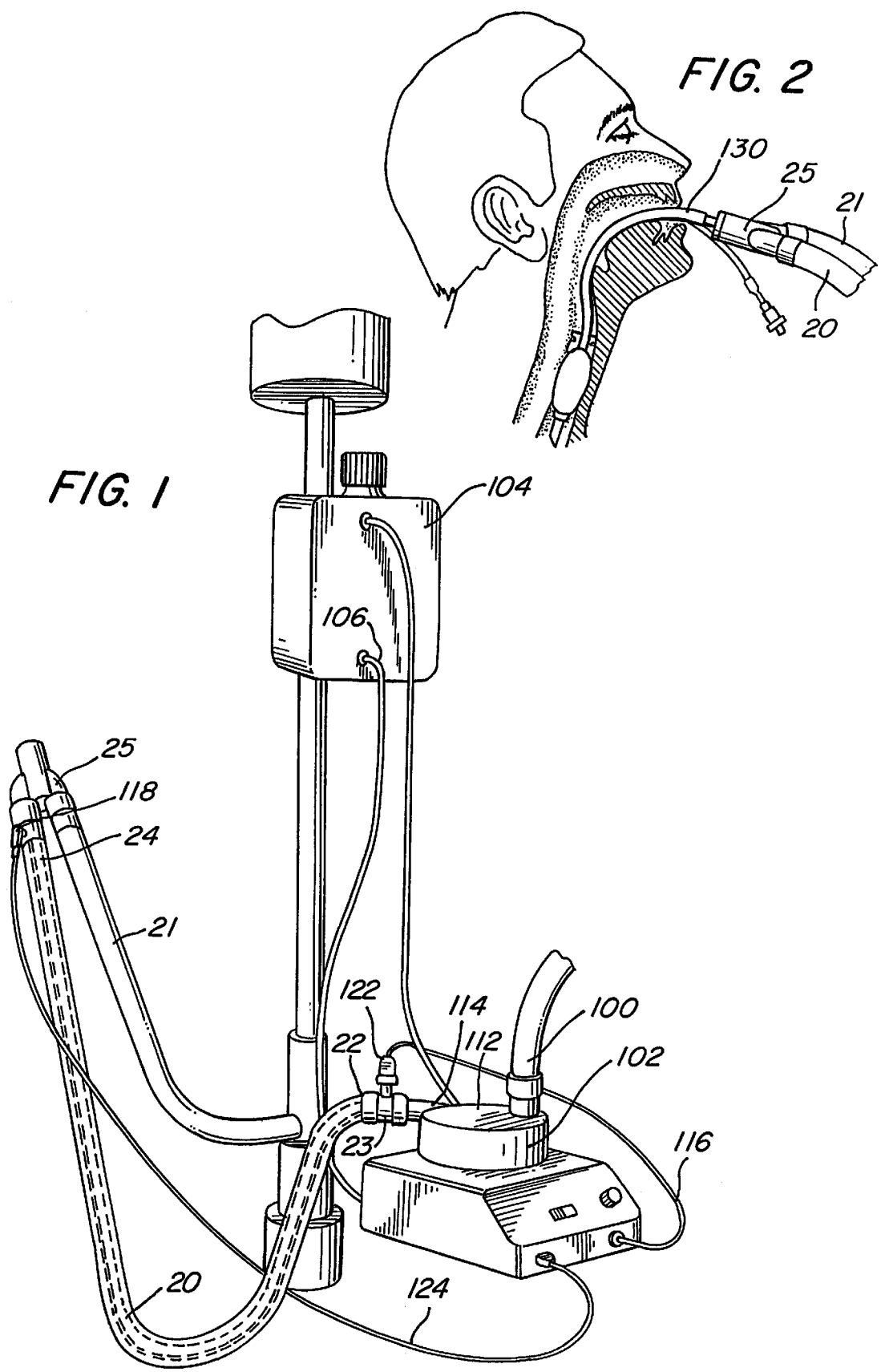

MEDICAL AIR HOSE INTERNAL FLOW HEATER

BACKGROUND OF THE INVENTION

1. Field of the Invention

The present invention is related generally to temperature and/or humidity control in a conduit for communicating a gas such as air or oxygen to a medical patient, and more particularly to a tubing with an internal heating element to control the temperature and humidity of the gas therein prior to delivery to a patient.

2. Description of Related Art

Systems are currently in use to aid in the delivery of air or other gases to patients who cannot breathe on their own for various reasons. The human upper airway is a location where inspired air is heated and humidified before passing through the trachea to the lungs. Patients who cannot breathe on their own require the assistance of a ventilator. Air delivered from a ventilator is typically dry, coming from a compressor or liquid oxygen source. When this air is delivered to a patient whose upper airway is bypassed, the mucous layer and sensitive tissues of the lower airway is dried out and an additional metabolic demand is required of the patient to warm the air to body temperature. Patients on long term ventilation without humidification develop mucous plugs in the lower airway, requiring interventional suctioning and may develop damage to the lower airway tissues which may exacerbate drying of the airway. Increased metabolic demand places additional strain on all physiologic systems and threatens patient outcome. Consequently, ventilatory air is often heated and humidified prior to being delivered to patients on ventilatory support where the upper airway is bypassed with an endotracheal or tracheostomy tube.

Conventional ventilator air humidification consists of warming water to an elevated temperature and passing an inspired air flow over or through the warm water to pick up the available humidity and equilibrate the resultant water vapor/air mixture to the humidifier temperature. The inspired air is conducted to the patient through a ventilator circuit hose or tube, typically a corrugated polyethylene hose, which is in communication with the endotracheal or tracheostomy tube. The interconnecting hose is designed to provide a low resistance, lightweight, highly flexible flow channel such that inspiration does not require excessive effort. The hose is adapted to mate with a mask or endotracheal or tracheostomy tube where the air can be delivered to the patient.

Since the ventilator circuit hose typically has a relatively thin wall and a large surface area due to the corrugations, significant heat transfer occurs between the heated flow and the relatively cooler ambient air surrounding the hose. As the heated air travels along the hose, some heat is lost to the air outside of the hose resulting in a temperature drop in the air flow. The drop in temperature in the humidified air flowing through the hose reduces the capacity of the air to suspend the moisture, causing some of the moisture to precipitate out along the length of the tube. This reduction in the humidity of the airstream as the air cools leads to a collection of water in the corrugations of the tube. The condensed water poses a particular hazard to the patient if it accumulates in sufficient quantity to trickle into the endotracheal or tracheostomy tube, where it may be introduced into the lungs. In addition, the water collecting in the warm hose forms a fertile breeding ground for bacteria which can cause airway infections. Lastly, the drop in temperature creates an uncertainty in the temperature of the air being delivered to the patient in addition to the temperature of the air leaving the ventilator.

To reduce the precipitation of water and maintain a suitable air temperature, electrically heated hoses have been used to add additional heat to the flowing air, counteracting the heat lost along the length of the hose. Conventional electrically heated hoses or tubing employ a heating element, in the form of a solid or stranded resistance wire, that is either embedded in the wall or wound around the circumference of the hose. In some cases, the resistance wire is spirally wrapped around a supporting thread before it is wrapped around the hose. These hoses apply heat at the walls, which is communicated to the fluid passing within the hose by convection. Alternatively, the heating element may be loosely strung within the lumen of the hose. In this case, heat is conducted to the fluid passing within the lumen from the heating element through insulation placed over the heating element.

A problem particular to spirally wound heater wire elements is the formation of localized hot spots from variations in power density. The variation in power density is caused by inconsistency of the spiral pitch over a short section of the element. The winding pitch seems to be particularly difficult for manufacturers of this element to maintain and necessitates specialized testing and equipment to detect in a high speed extrusion operation. This localized hot spot can melt through the hose wall and pose a fire threat.

OBJECTS AND SUMMARY OF THE INVENTION

It is a first object of the present invention to provide a heater for a flexible tubing which overcomes the drawbacks of the prior art and improves the delivery of gases at a prescribed temperature and humidity.

It is another object of the present invention to provide a heater which reduces the occurrence of tubing failure due to burn-through.

It is another object of the present invention to provide a heater which is adaptable to currently gas delivery systems.

It is yet another object of the present invention to provide a heater which heats gases more efficiently than prior heating systems.

The objects of the present invention are achieved using a flexible tubing having an elongate flexible plastic ribbon disposed inside the tubing generally along a center region and extending predominantly the length of the tubing, and a heating element carried by the ribbon to heat the air. A preferred embodiment of the present invention uses a temperature gage at the point of delivery which is used to adjust the heater to maintain the temperature of heated and humidified air at the point of delivery to the patient.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 is a perspective view of a humidifying system including humidified air generation for use with a preferred embodiment of the present invention.

FIG. 2 is a side view, partially cut-away, of an endotracheal tube connected to the heated tubing;

DETAILED DESCRIPTION OF THE PREFERRED EMBODIMENTS

Figure 3:
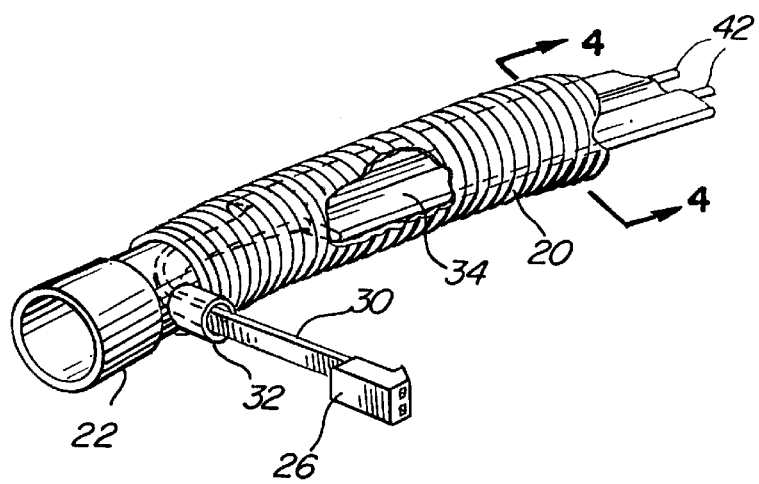
FIG. 3 is an elevated perspective view, partially cut away of a preferred embodiment of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a heater for use with flexible tubing especially suited for delivering heated, humidified air to a patient.

An embodiment of a system for delivering heated air using the present invention is illustrated generally in FIG. 1. A flexible corrugated tubing 20 made of polyethylene or other suitable material provides a channel for humidified air, which is delivered to a patient. The flexible tubing 20 is connected at a tubular adapter 23 to an air humidifying machine 102 while a second end 24 is connected at a "Y" adapter 25 to an endotracheal tube (see FIG. 2) or tracheostomy tube, or in some cases, a mask to be placed over the patient's mouth. The air humidifying machine 102 heats and moisturizes air to conditions which are suitable for the patient to accept.

Referring to FIG. 1, a water supply reservoir 104 is connected to a tube 106 which feeds water to a heated platen (not shown) within the air humidifying machine 102. The heated platen is housed in a chamber 112, and the platen elevates the water temperature to liberate a sufficient amount of vapor into the chamber 112. An air supply hose 100 connected to a ventilator (not shown) delivers the air (or other gas to be delivered) into the chamber 112 where it encounters the water vapor. The air coming into the chamber 112 mixes with the water vapor and is heated by the presence of the water vapor to a temperature which is controlled by the temperature of the platen. The air leaves the chamber 112 heated and "humidified" at exit port 114 and connects to the adapter 22 of the tubing 120.

At the entrance of tubing 20 is a connector 26 (see FIG. 3) which mates to an interconnecting connector 122 and electrical cable 116 from the controller/monitor of the humidifying machine 102 to receive an electrical voltage from the controller/monitor. The connector 26 is tethered by a strip 30 that extends from or is mounted to a port 32. The connector 26 is electrically connected to a heating element 42 supported by or within a ribbon 34. As described more fully below, the flexible ribbon 34 supports the heating element 42 which is used to control the temperature and humidity inside the tubing 20.

Figure 4:
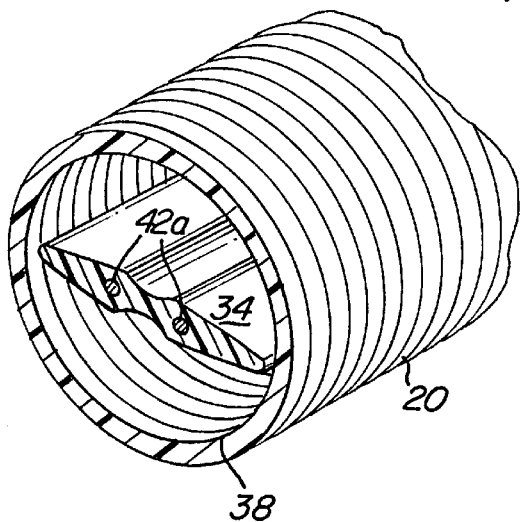
FIG. 4 is a perspective cross-sectional view taken along the indicated line in FIG. 3.

The tubing 20 receives the humidified air from the chamber 112 and the air flows along the length of the tubing. The tubing 20 contains within its interior the plastic ribbon 34 which is flexible enough to bend with the tubing 20, but rigid enough to maintain its flat, solid profile upon bending. The flexible ribbon 34 has a profile (see FIG. 4) which extends up to the inner wall 38 of the tubing 20 with enough tolerance to allow the elongated flexible ribbon 34 to be slid in and out of the tubing 20, but maintains the flexible ribbon 34 centered within the tubing 20. Other profiles are possible for the flexible ribbon 34, such as triangular profile with three spokes, but the planar profile as shown in FIG. 2 is generally preferred because it provides better flexibility than more complicated profiles. The flexible ribbon 34 is preferably made of a plastic material with a relatively high melting point, the preferred plastic material being polyethylene similar in formulation to the composition of the hose material.

Figure 5:
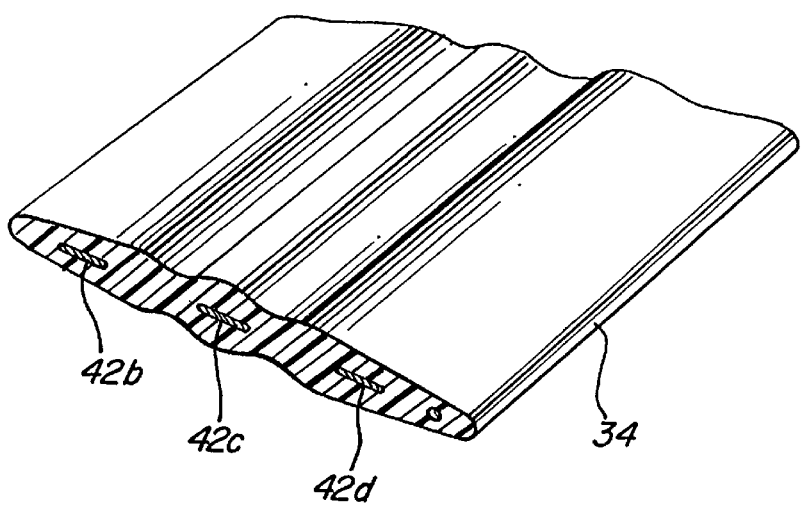
FIG. 5 is a perspective, cross-sectional view of a flexible ribbon of the present invention illustrating a heating element therein.

The flexible ribbon carries a heating element 42 near the center of its profile which is used to heat the flow traveling in the tubing 20. The heating element 42 is preferably in the form of a solid resistance wire carried on or in the flexible ribbon 34. The heating element 42 may be located on top of the flexible ribbon 34, or in a preferred embodiment the heating element 42 is extruded in the flexible ribbon (FIG. 4) as long as the ribbon is thin enough to conduct the heat generated by the heating element to the flow. A single wire 42a may be used to traverse the length of the flexible ribbon 34, or a plurality of wires 42b, 42c, 42d may be used (see FIG. 5). Wires 42 or other electrically conductive elements supported by the ribbon 34 can be connected in a series or in parallel, or combination of series and parallel connections in order to make up a desired total heater circuit resistance. The heating element or elements 42 preferably start and terminate at a single end to form a loop or loops along the flexible ribbon 34 such that a power source can be connected at the single end.

As described above, the heating element 42 is connected to an electrical power supply within the air humidifying machine 102 via cable 116 (see FIG. 1). Voltage is applied creating an electrical current in the heating element, which in turn generates heat due to the resistance of the wire. The heat energy generated by the heating element 42 is transferred to the humidified air traveling along the tubing 20. If more voltage is applied to the heating element 42, then more heat energy will be supplied to the load, and the amount of heat can be adjusted to maintain the proper temperature of the air at the exit 24. Having the heating element 42 extend the length of the tubing permits heating of the air right up to delivery to the patient and reduces the likelihood of condensation of the humidified air. To further control the temperature of the air being delivered to the patient, a temperature probe 118 may be placed at the Y connector 25 at the exit 24 of the tubing 20 to measure the exit temperature of the air delivered to the patient. The temperature is communicated via cable 124 to the controller/monitor within the humidifying machine 102, which then adjusts the power supplied to the heating element 42 or heated platen in order to maintain the desired exit temperature.

The tubing terminates at a "Y" juncture 25 or alternately a "T" joint, which is preferably plastic, and the Y juncture is connected to a delivery apparatus such as an endotracheal tube 130 as shown in FIG. 2. Other delivery systems are possible, such as breathing masks and tracheostomy tubes, and operation of each of these delivery systems are well known in the art.

The air being expelled by the patient is carried away by a tubing 21 which may also include a heating element similar to tubing 20. This is because the air taken away from patient is humidified, and the same risks of condensation such as bacteria build-up and maintenance are present in the evacuation side of the tubing.

The present invention is advantageous over the prior art loose heating element in several ways. Pseudo-laminar air flow exists within the hose where the majority of flow occurs close to the center of the hose cross section. A velocity profile of the flow in the tubing 20 would also show a maximum velocity along the center region of the tubing, decreasing radially to a minimum at the tubing wall 38. The location of the heating element 42 in the center of the air flow assures that the heat is being conducted more efficiently to the air flowing through the lumen. The efficiency of the heat exchange by the heating element 42 to the air flow is enhanced by promoting heat exchange where most air travels. Without a support for the heating element, such as the flexible ribbon of the present invention, the position of the heating element cannot be guaranteed to lie at the center of the tubing and insufficient heat transfer occurs where the heater lies close to or against the internal hose wall. This results in more heat energy transferred to the tubing wall than the air and localized condensation may occur. Additionally, the location where the heating element touches the wall becomes a site of dangerous melt through and possible ignition.

In the present invention, however, the heating element 42 is held away from the ventilator circuit hose wall 38 and near the center of the air flow by the supporting ribbon 34. The temperature of a high dissipation location at a high air flow location is minimized because heat is spread across the supporting ribbon by conduction and convected away by the surrounding air. The possibility for melting the hose or heater insulation is therefore minimized by supporting the heating element 42 in the center of the air stream where the dissipation is spread and transfer of energy is maximized.

In an alternate embodiment, the heating element may be resistance wire that is spiral wound over a supporting element and extruded in a similar plastic support structure. Construction and electrical connections are similar to the previous embodiment. It should also be recognized that the heat transfer and electrical connections can be realized with resistance elements in the form of conductive bands, etched foils in straight or serpentine patterns, or conductive films applied or embedded in the ribbon. The ribbon can be removably disposed in the tubing, fixedly disposed or integrally formed with the tubing. Additionally, the ribbon can be mechanically extruded with the tubing as an integral unit.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A flexible tubing heating system for delivering a gas at a controlled temperature from a source to a recipient person comprising:

a flexible hollow tubing having a generally circular cross-section, including an inner wall defining an interior region;

an elongated, flat, solid, flexible insulating ribbon disposed within said tubing and extending substantially from a proximal end at said source to a distal end near said recipient, said ribbon having first and second edges adjacent the inner wall and a middle portion positioned within the central interior region of said tubing; and electrical unit within said ribbon and spaced from said inner wall for heating the gas as the gas travels from the proximal end to the distal end to prevent formation of liquid in the flexible tubing.

2. The heating element of claim 1 wherein said ribbon is fixedly disposed in said tubing.

3. The heating element of claim 2 wherein said ribbon is integrally formed with said tubing.

4. The heating element of claim 3 wherein said ribbon is mechanically extruded with said tubing to form an integral unit.

5. The flexible tubing of claim 1 wherein said electrical unit for heating the gas comprises an electrically conductive wire.

6. The flexible tubing of claim 5 wherein said electrically conductive wire is mechanically extruded in said ribbon.

7. The flexible tubing of claim 1 wherein said electrically conductive wire extends along said ribbon from the proximal end to the distal end and back to the proximal end such that an electrical circuit can be formed at the proximal end of said ribbon.

8. The flexible tubing of claim 5 wherein said electrical unit for heating the gas comprises a plurality of electrically conductive wires extending generally from the proximal end of said ribbon to the distal end of said ribbon.

9. The flexible tubing of claim 1 wherein said track is made of polyethylene.

10. The flexible tubing of claim 1 wherein said electrical unit for heating the gas comprises an electrically conducting band supported by said ribbon.

11. The flexible tubing of claim 1 wherein said electrical unit for heating the gas comprises an electrically conductive film supported by said ribbon.

12. The flexible tubing of claim 1 wherein said electrical unit for heating the gas comprises an electrically conductive etched foil supported by said ribbon.

13. The flexible tubing of claim 1 wherein said ribbon is removably disposed in said tubing.

14. An improved system for delivering a heated humidified gas to a medical patient comprising:

means for generating a humidified gas;

means for moving said humidified gas through a flexible conduit;

a flexible conduit having an inner wall, said flexible conduit connected at a first end to said means for generating a humidified gas;

a heating element disposed within, and generally spanning said flexible conduit, said heating element spaced from said inner wall of said flexible conduit such that heat is transferred to a flow of air where a velocity of said air is greatest, the heating element comprising:

an elongated flat, solid, flexible ribbon of insulating plastic having a width that extends through the inner central region and a heat generating element within the solid ribbon for providing sufficient heat to prevent the humidified gas from depositing a liquid in the flexible conduit.

15. A flexible tubing for delivering a humidified gas at a controlled temperature from a humidifier to a recipient person, consisting of:

a flexible corrugated hollow tubing having an inner wall defining an interior region;

an elongated flat, flexible, solid insulating plastic ribbon of a width approximately the width of the tubing and positioned within the inner wall so that a central portion of the ribbon lies on a centric position of the hollow tubing; and an electrical heat generating member extending along and within the ribbon for heating the humidified gas to prevent formation of liquid in the flexible tubing.

16. The flexible tubing of claim 15, wherein the solid ribbon is a polyethylene resin.

17. A system for delivering a humidified gas at a controlled temperature, consisting of:

a humidifier for providing a humidified gas;

a flexible corrugated hollow tubing having an inner wall defining an interior region and connected at one end to the humidifier for receiving the humidified gas;

an elongated flat, flexible, solid ribbon of a width approximately the width of the tubing and positioned within the inner wall so that a central portion of the ribbon lies on a centric position of the hollow tubing; and an electrical heat generating member extending along and within the ribbon for heating the humidified gas to prevent formation of liquid in the flexible tubing.

\* \* \* \* \*